Figure 3B:
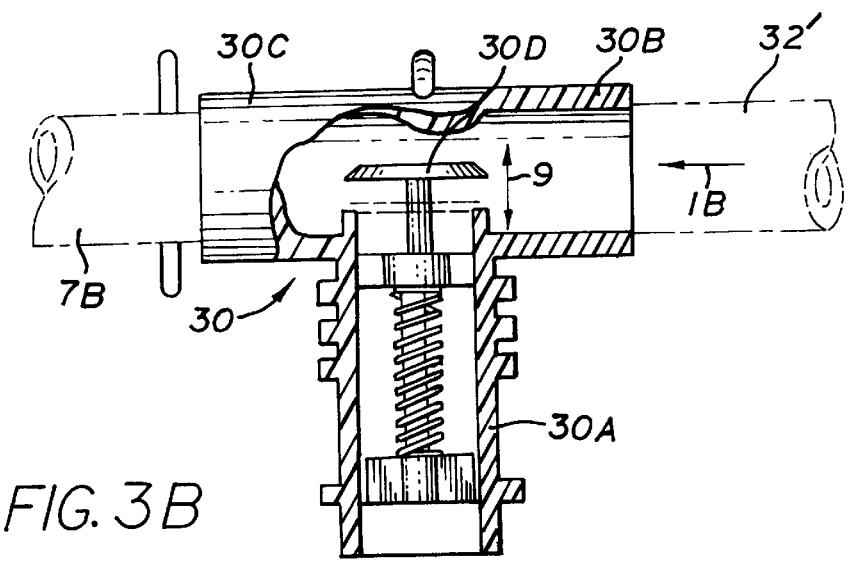
Figure 3C:
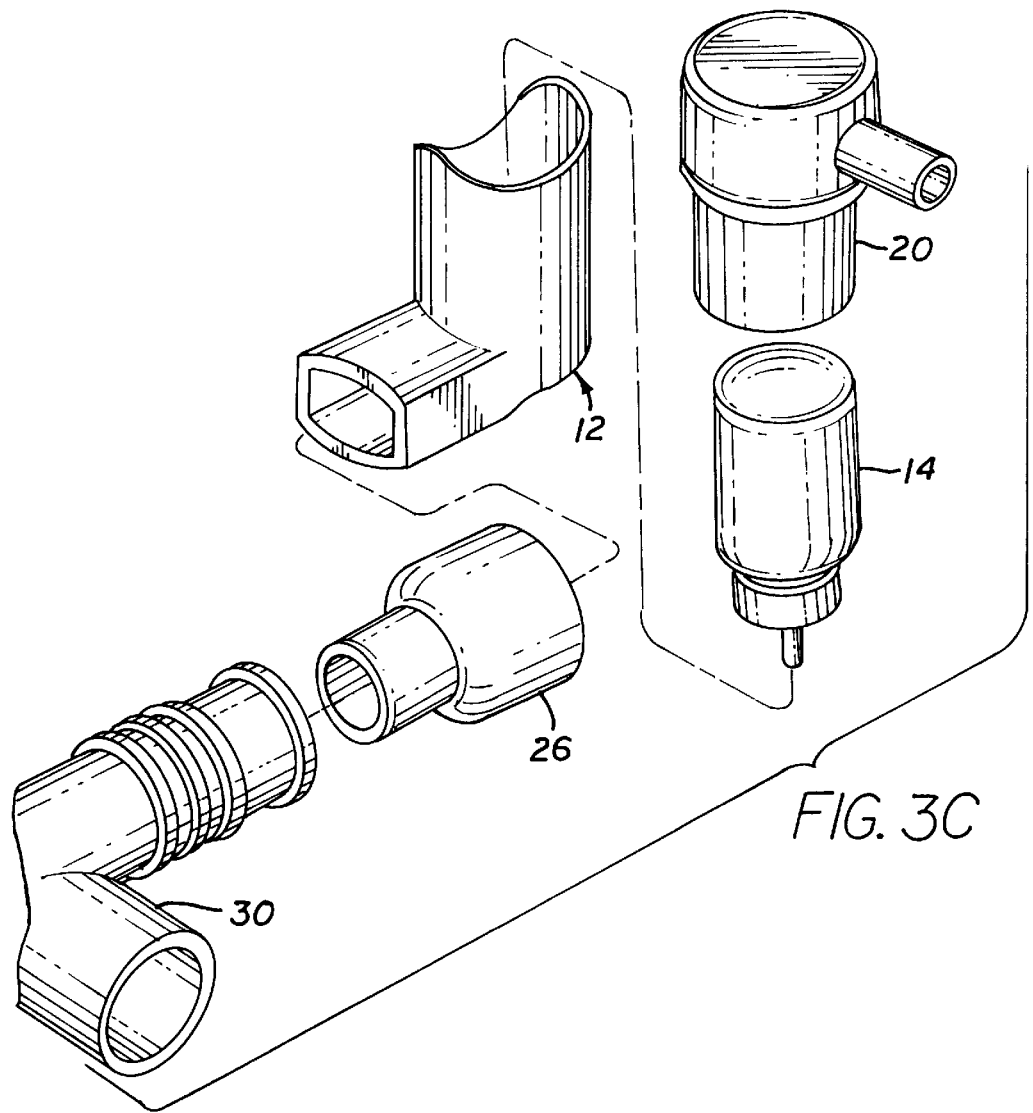

United States Patent [19]
Sladek

[11] Patent Number: 6,014,972
[45] Date of Patent: Jan. 18, 2000

[54] DRY DRUG PARTICLE DELIVERY SYSTEM AND METHOD FOR VENTILATOR CIRCUITS

[75] Inventor: David T. Sladek, Tucson, Ariz.

[73] Assignee: Thayer Medical Corporation, Tucson, Ariz.

[21] Appl. No.: 08/989,085

[22] Filed: Dec. 11, 1997

[51] Int. Cl.[7] ................................................. A61M 15/00
[52] U.S. Cl. ................. 128/203.12; 128/203.15
[58] Field of Search ........................ 128/203.12, 203.15, 128/203.21, 200.21, 200.22, 203.28, 207.14, 200.24, 202.27

[56] References Cited

U.S. PATENT DOCUMENTS

| | | | |
|---|---|---|---|
| 4,951,661 | 8/1990 | Sladek | 128/202.27 |
| 5,474,058 | 12/1995 | Lix | 128/200.18 |
| 5,546,930 | 8/1996 | Wikefeldt | 128/201.13 |
| 5,720,282 | 2/1998 | Wright | 128/207.14 |
| 5,769,073 | 6/1998 | Eason et al. | 128/203.15 |

*Primary Examiner*—John G. Weiss
*Assistant Examiner*—Charles W. Anderson
*Attorney, Agent, or Firm*—Cahill, Sutton & Thomas P.L.C.

[57] ABSTRACT

A system for introducing a dose from a metered dose inhaler canister into the inspiratory stream (1B) of a ventilator system including an inspiratory tube (32), a Y connector (3), and an endotracheal tube (7) intubated in a patient, including a valved T connector (30) having a valved port (30A) and first (30B) and second (30C) ports coupled to conduct the inspiratory stream (1B) through the valved T connector, an MDI canister (14), and a nozzle adapter structure (31) having a first port (31A) for insertion into the valved port (31A) to open a valve thereof and a nozzle (31B) receiving a stem (14A) of the MDI canister (14) and ejecting a plume (17) of MDI medication particles upon activation of the MDI canister. A dry gas inlet (31D) receives dry gas which flows through the nozzle adapter structure (31) into the valved port (30A) and into the inspiratory stream (1B), and carries the plume from the nozzle adapter structure (31) through the valved port (30A) into the inspiratory stream (1B).

13 Claims, 4 Drawing Sheets

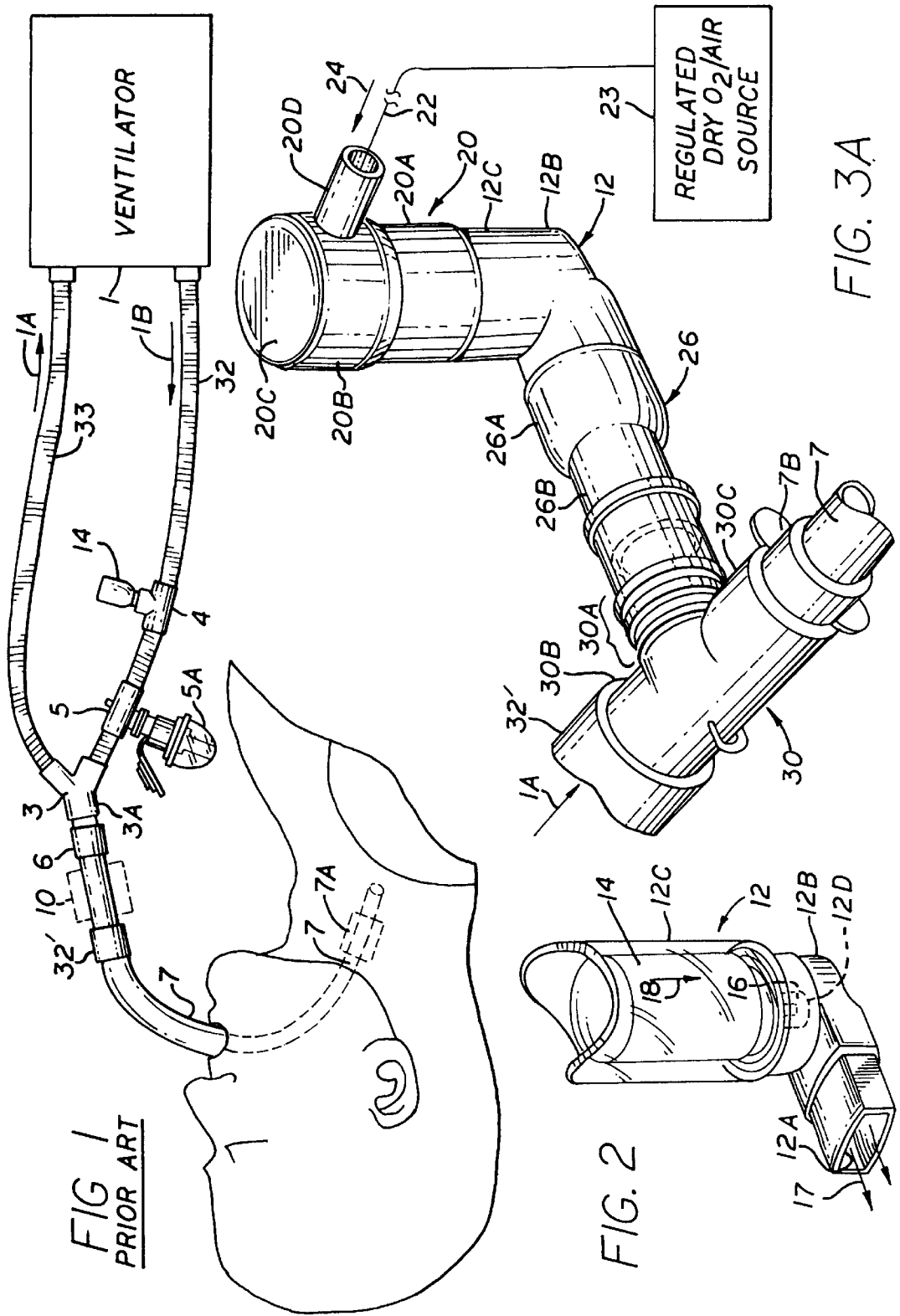

U.S. Patent    Jan. 18, 2000    Sheet 3 of 4    6,014,972
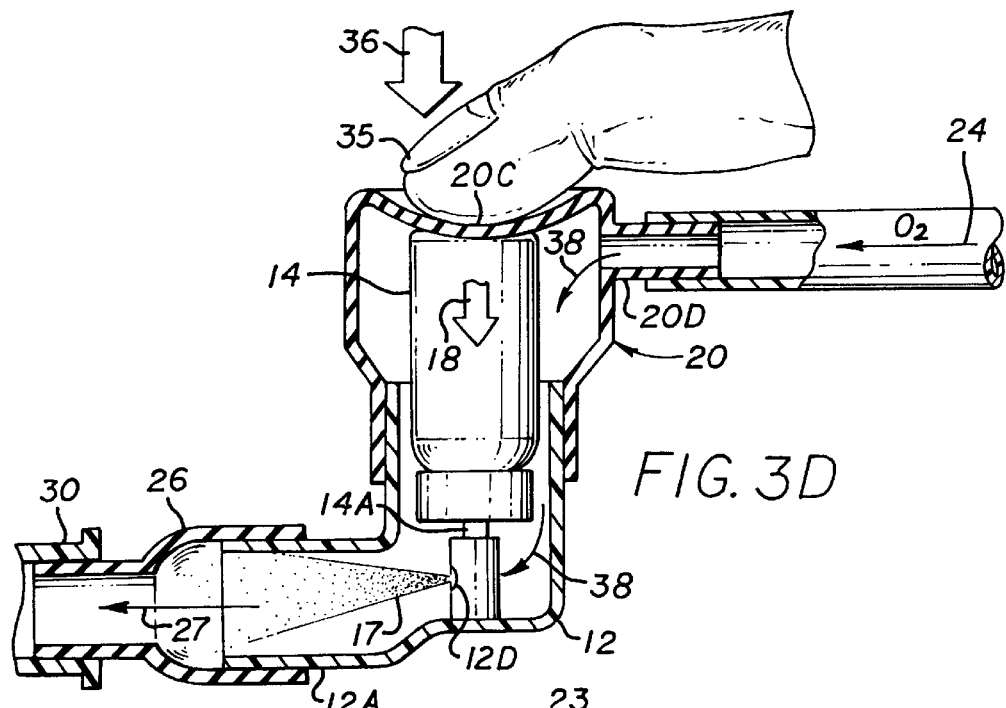
FIG. 3D
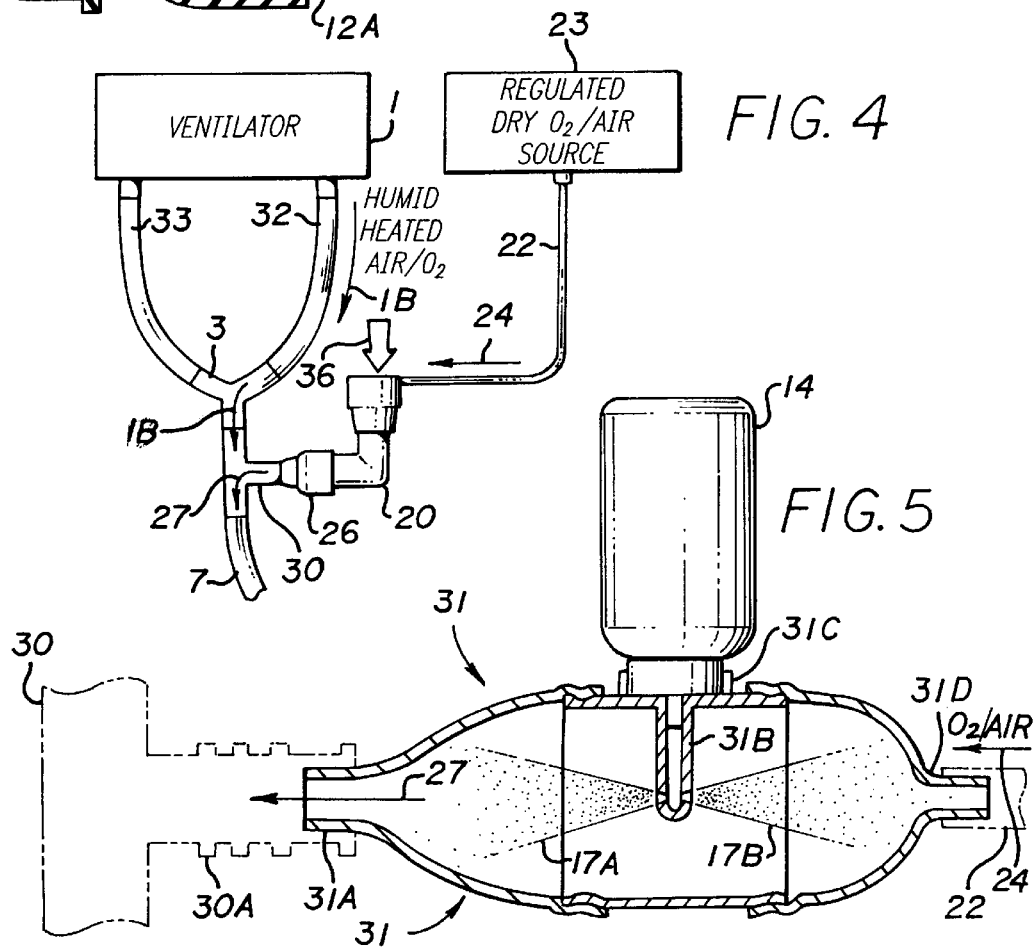
FIG. 4
FIG. 5

DRY DRUG PARTICLE DELIVERY SYSTEM AND METHOD FOR VENTILATOR CIRCUITS

BACKGROUND OF THE INVENTION

The invention relates to a device for delivering dry medication particles from an MDI (metered dose inhaler) or dry powder medication measuring device to an intubated patient through a ventilator circuit or an anesthesia device, and more particularly to a device which reduces or minimizes absorption of humidity by minute, dry, light medication particles and thereby prevents them from gaining weight and falling out of the inspiratory airstream before they reach their targeted sites.

In prior devices for the administration of aerosol medication to intubated patients, the aerosol is delivered directly into tubing of a ventilator and carried with air or oxygen into the patient's lungs. FIG. 1 shows a typical ventilator circuit, including a ventilator 1 having an expiratory tube 33 by means of which air is expelled as indicated by arrow 1A from the lungs of a patient through an endotracheal tube 7 into a Y connector 3, an expiratory tube 33 and into ventilator 1. Ventilator 1 also forces a measured regulated inspiratory stream 1B of air or oxygen through an inspiratory tube 32, a valved T connector 5 of the type disclosed in U.S. Pat. No. 4,951,661, Y connector 3, and endotracheal tube 7 into the lungs of the patient, to thereby provide ventilation, i.e., assisted breathing. In some cases, a heated wire (not shown) extends through inspiratory tube 32 to heat the inspiratory stream 1B, which usually is humidified, to thereby prevent cooling of the inspiratory stream and resulting condensation of moisture from it onto the walls of the inspiratory path. (Typically, ventilator 1 includes a humidifying device for inspiratory stream 1B, since ordinarily it is harmful to provide dry air or oxygen to the lungs of a patient.)

Commonly, a passive humidifier 6 such as a "heat and moisture exchanger" (HME) or "hygroscopic condenser humidifier" (HCH) air filtering and humidifying device is coupled between one port of the Y connector 3 and the proximal end of endotracheal tube 7. Frequently, an adapter 4 is coupled in line with inspiratory tube 32 to allow aerosol medication from an MDI canister 14 to be introduced into the inspiratory air or oxygen stream 1B. The adapter 4 includes a nozzle that ejects an expanding aerosol plume when the MDI canister 14 is actuated. The aerosol plume produced by MDI aerosol canister 14 includes very finely divided medication particles, typically in the 1–10 micron diameter range. Inside the MDI canister 14, such medication particles are suspended in a pressurized liquid propellent. Upon actuation, a metered dose of the suspension is injected through the outlet stem of the canister through the nozzle of the adapter 4 to form the expanding plume. The drug-bearing liquid propellent breaks up into small droplets, which must evaporate to release the dry 1–10 micron medication particles. As the aerosol plume from MDI canister 14 is ejected into the inspiratory stream 1B, the released, dry, very light medication particles are carried in the humid air or oxygen inspiratory stream 1B for the brief time required to reach the intended therapeutic sites inside the patient's lungs. Drying of medication particles carried by the liquid propellant may be impeded by humidity in the inspiratory airstream.

The released medication particles are light enough to be efficiently carried by the inspiratory air stream 1B through the curved path defined by the inspiratory apparatus into the patient's lungs. The medication particles may be hygroscopic, and hence may absorb water molecules and grow in size and weight as they travel through the moisture-laden inspiratory airstream 1B. In that case, droplets formed around the medication particles become relatively heavy, and many of them therefore have a tendency to "fall out" of the inspiratory stream 1B by impinging on and coalescing on the walls of the tubing and bronchi, and therefore not reach the therapeutic sites in the patient's lungs.

When dry powder drug dispensing devices are used, the humidity of the inspiratory air stream 1B is not conducive to efficient dispersion and effective delivery of the dry powder to the therapeutic sites in the patient's lungs, especially if the powder is hygroscopic and results in condensation of droplets on the medication particles, which gain weight and then impinge on the walls of the tubing or upper bronchi and are lost from the quantity of medication intended to be carried to the lungs of the patient. Therefore, the effective medication dose is reduced for either MDI medication or dry powder medication.

Another problem of the prior art arises in ventilation circuits which include a "heat and moisture exchanger" (HME) or a "hygroscopic condenser humidifier" (HCH) 6 connected with the Y connector, plus an aerosol medication delivery device in the inspiratory path 1B. This arrangement necessitates removing the HME or HCH 6 from the ventilator circuit to allow the individual medication particles carried by inspiratory stream 1B to reach the proximal end of the endotracheal tube 7. This interruption of the inspiratory stream 1B is undesirable, as it may expose the patient or caregiver and the interior of the tubing and ventilator to airborne bacteria and/or viruses.

In another arrangement of prior art, introducing the aerosol or dispersed dry drug material downstream from the HME or HCH can result in undesirable increasing of the "dead-volume" air, i.e., air which is rebreathed by the patient.

Yet another problem of the prior art devices is that none of them allow an MDI drug to be introduced into the ventilator circuit by means of the nozzle of the same inhaler or delivery system which is provided with the MDI canister by the drug supplier. Consequently, the MDI canister 14 must be removed from the manufacturer's inhaler nozzle and separately inserted into the nozzle of the ventilator adapter 4.

There clearly is an unmet need for a method of providing delivery of MDI medication into a ventilator circuit using the same nozzle supplied by the manufacturer.

SUMMARY OF THE INVENTION

Accordingly, it is an object of the invention to provide a delivery system for delivering drug medications from an MDI canister or a dry powder delivery system that reduces the initial exposure of dry, minute medication particles to moisture, and thereby prevents condensation of moisture on and hence formation of droplets around the medication particles, to prevent them from gaining weight and then falling out of the inspiratory stream before reaching therapeutic sites in the patient's lungs.

It is another object of the invention to allow introduction of MDI aerosol medication directly from various MDI canister suppliers' inhaler nozzles into the inspiratory stream of a ventilator system.

It is another object of the invention to provide a system for delivery of MDI aerosol medication particles or dry medication particles without requiring opening of the ventilator circuit, even when a passive humidifier is in place at the Y connector.

It is another object of the invention to provide a system for delivery of MDI aerosol medication particles or dry powder medication particles that reduces "dead volume" of air which is rebreathed by a patient, when the delivery device is in place between the Y connector and the endotracheal tube.

Briefly described, and in accordance with one embodiment thereof, the invention provides a tapered elastomeric adapter (26) to connect the mouthpiece of an MDI aerosol inhaler into a valved T connector permanently installed in the respiratory tube of a ventilator circuit, and an elastomeric end cap (20) that includes a port (20D) for dry gas to flow from an external pressurized source (23), around the MDI canister and out of the MDI mouthpiece and thereby carry the plume of dry MDI medication particles into the ventilator circuit by way of the valved T connector. The valved T connector is constructed to have low dead volume, i.e., it minimizes the inspiratory path volume between the endotracheal tube and the Y connector when the plume of dry MDI medication particles is introduced at the endotracheal tube. In this case, the valved T connector is fitted between the Y connector (3) and an endotracheal tube (7). However, the valved T connector also can be used in-line, and also works with nebulizers.

A tapered end of the elastomeric adapter (26) is designed to fit snugly into the lower inlet of the valved T connector (30), thereby opening its valve automatically and allowing the aerosol drug to be introduced into the ventilator circuit. Another wider end of the elastomeric adapter (26) is fitted tightly over the mouthpiece (12A) of the inhaler supplied by the manufacturer of the MDI canister (14). Once in place over the mouthpiece, the tapered elastomeric adapter (26) provides a way of connecting the drug manufacturer's inhaler nozzle to the valved T connector so the MDI canister can be actuated to introduce an aerosol medication plume into the inspiratory stream (1B) of the ventilator. The elastomeric end cap (20) is tightly fitted over the top end of the manufacturer's inhaler, forming a seal over both the top of the inhaler and the MDI drug canister. The end cap has an outlet port (20D) or hose connector for the external dry gas source, such as pressurized air or oxygen. Just before the MDI drug canister is actuated by pressing on a top flexible membrane of the elastomeric end cap through which the canister is depressed to actuate it, the flow of dry gas from the pressurized source (23) is caused to flow between the canister (14) and inner walls of the manufacturer's inhaler (12). This provides a bolus of dry gas to carry the expanding plume of medication particles as the aerosol evaporates. Therefore, the medication particles are more likely to be carried dry into the target areas of the lungs instead absorbing moisture, gaining weight, and impinging on inner walls of inspiratory path/tubing or upper bronchi. When the aerosol treatment has been completed, the tapered elastomeric adapter is withdrawn from the valved T connector, causing the valve to close automatically, to thereby maintain a closed ventilator circuit. The compressed gas source (23) then is disconnected from the inlet port (20D).

BRIEF DESCRIPTION OF THE DRAWINGS

FIG. 1 is a diagram illustrating a conventional connection of a ventilator to an endotracheal tube intubated into a patient.

FIG. 2 is a perspective view of a conventional manufacturer's MDI inhaler device.

FIG. 3A is a perspective view illustrating the medication particle delivery system of the present invention.

FIG. 3B is a section view of the valved port 30A of the valved T device 30 shown in FIG. 3A.

FIG. 3C is an exploded view of the system shown in FIG. 3A.

FIG. 3D is a section view illustrating actuation of the MDI canister in the MDI drug delivery system of FIG. 3A.

FIG. 4 is a diagram useful in explaining the operation and air flow in the inspiratory path of the drug delivery system of the present invention.

FIG. 5 is a section view of an alternative technique according to the invention for introducing medication from an MDI canister into an inspiratory stream of a ventilator circuit.

FIG. 6A is a top plan view illustrating a substitute device for connecting the medication particle delivery system of the present invention into the inspiratory stream of FIG. 3A.

FIG. 6B is a section plan view of the device shown in FIG. 6A.

FIG. 7 is a side elevation view illustrating use of a spacer in the arrangement of FIG. 3A.

DETAILED DESCRIPTION OF THE PREFERRED EMBODIMENT

Referring to FIG. 2, a conventional MDI drug delivery system or MDI inhaler 12 includes a plastic corner section 12B with an integral mouthpiece 12A. An upper hollow, cylindrical "boot" section 12C is attached at a right angle to mouthpiece 12A by corner section 12B. As partly shown by dotted lines, MDI inhaler 12 includes a conventional MDI canister 14 within the boot 12C so that its stem is inserted into a nozzle 12D in the corner section 12B. When the canister is depressed as indicated by arrow 18, the nozzle 12D ejects a measured dose of medication from MDI canister 14 in the form of an expanding aerosol medication plume 17 in which the liquid propellant rapidly evaporates, leaving dry, light, 1–10 micron medication particles (which are easily carried by an air stream).

Referring to FIG. 3A, and also to FIG. 3C which shows an exploded view of the arrangement of FIG. 3A, the medication delivery system of the present invention includes a valved T connector 30, which can be of the type described in commonly assigned U.S. Pat. No. 4,951,661 (Sladek), incorporated herein by reference, connected in fluid communication with inspiratory tube 32. FIG. 3B shows the basic structure of valved T connector 30. When the coupling port 26B of elastomeric adapter 26 is inserted into valved port 30A, the valve plate 30D therein automatically opens to allow a medication plume to be safely introduced through the valved port 30A into the inspiratory stream 1B. When the coupling port 26B is withdrawn, the valve plate 30D automatically closes, to allow positive pressure to be maintained in the inspiratory path and prevent airborne contamination from entering it.

Referring again to FIG. 3A, a nose portion 26B of an elastomeric adapter 26 is positioned in the valved port 30A of valved T connector 30 to introduce MDI aerosol medication (or dry powder medication) into the inspiratory airstream 1B in the inspiratory tube 32. Inspiratory tube 32 is connected to Y connector 3 as shown in FIG. 1. The main port 3A of Y connector 3 is connected by a piece of tubing 32' (FIG. 3A) to an inlet section 30B of valved T connector 30. Dotted line 10 in FIG. 1 indicates the preferred location of valved T connector 30 in the ventilator system in accordance with the present invention. An adapter or connector 7B of endotracheal tube 7 of FIG. 1 is connected to the outlet port 30C of valved T connector 30, the operation of which is thoroughly described in the above-mentioned U.S. Pat. No. 4,951,661. As shown in FIG. 3A, an enlarged portion 26A of elastomeric adapter 26 is connected to the mouthpiece of MDI inhaler 12 (or any of a number of commercially available inhalers that are similar to inhaler 12 as shown in FIG. 2).

An elastomeric end cap 20 has a mouth section 20A that fits tightly over the open end of boot portion 12C in which the MDI canister 14 (FIG. 2) is positioned. Elastomeric adapter 26 and elastomeric end cap 20 can be composed of a thermoplastic polymer or rubber such as the type marketed under the trademark KRATON by the Shell Chemical Company. An enlarged upper end portion 20B of elastomeric end cap 20 has an integral flexible top membrane 20C which can be easily depressed by the finger or thumb of a respiratory therapist or nurse in order to depress and thereby activate MDI canister 14 as indicated by arrow 18 in FIG. 2.

Referring to FIGS. 3A and 3D, the internal volume of elastomeric end cap 20 is in fluid communication with an integral dry gas inlet port 20D, which is coupled to a flexible dry air tube 22. Dry air tube 22 is connected to a regulated dry air or oxygen source 23. Arrows 24, 38 and 27 indicate the flow of dry oxygen through tube 22, inlet port 20D, elastomeric end piece 20, between MDI canister 14 and the wall of boot 12C, out of the mouthpiece 12A of inhaler 12, and into the open valved port 30D of valved T connector 30.

After the flow of dry oxygen or air indicated by arrow 24 has been initiated (typically at a flow rate of 8 to 15 liters per minute) so that dry oxygen or air is passing around the outer wall of MDI canister 14 as indicated by arrows 38, the respiratory therapist, after observing the operation of ventilator 1 and recognizing the beginning of an inspiratory cycle, and uses his/her thumb or finger 35 to depress the top membrane 20C of elastomeric end cap 20 as indicated by arrow 36.

Such depression of the top membrane 20C actuates MDI canister 14 as indicated by arrow 18, causing the nozzle assembly 12D into which the stem 14A of MDI canister 14 extends to eject plume 17 of liquid propellant droplets carrying the 1–8 micron medication particles. As previously mentioned, the propellant rapidly expands and evaporates, leaving the plume 17 to consist of dry, light 1–10 micron medication particles. The flow 27 of the bolus dry oxygen or air carries the plume 17 through elastomeric adapter 26 and into valved port 30A of valved T connector 30.

After a suitable amount of time (e.g., 5 seconds) has elapsed to allow the plume of MDI particles to be carried into the patient's lungs, the respiratory therapist then unplugs section 26B of elastomeric adapter 26 from valved port 30A to prevent more dry gas from entering the inspiratory stream 1A. The valve plate 30D in valved port 30A automatically closes when nose 30A is withdrawn, to thereby seal the inspiratory path from airborne contamination.

Referring to FIG. 4, the above-mentioned medication-carrying flow 27 from the regulated dry oxygen or air source 23 mixes with the humid, heated stream 1B forced by ventilator 1 through inspiratory tube 32. Typically, the flow rate of inspiratory air stream 1B may be from 25 to 125 liters per minute, so the 8–15 liters per minute flow of dry air from regulated dry air/oxygen source 23 appreciably reduces the humidity of the inspiratory stream 1B encountered by the dry MDI medication particles constituting plume 17 from which the propellant fluid has evaporated. Such reduction of humidity substantially reduces absorption by the dry medication particles of water from the moist inspiratory air stream 1B, preventing the medication particles from becoming weighted by formation of water droplets thereon. The inspiratory air stream 1B carries the dry, light medication particles and the bolus of dry air carrying them through endotracheal tube 7 all the way into the intended therapeutic sites within the patient's lungs, to minimize the loss of the medication dose due to medication particles becoming surrounded and weighted by droplets of water which impinge on the walls of the inspiratory path and fall out of the inspiratory stream before reaching the therapeutic sites in the patient's lungs.

Actually, it is believed that evaporation of all of the liquids, including liquid propellant (usually FREON) and water, from the medication particles to obtain "dry" medication particles which are most efficiently carried to the intended therapeutic sites in the lung of a patient, is a complex thermodynamic process that is not well understood. It is believed that as the liquid FREON is ejected from the MDI canister 14 to produce the initial expansion of plume 17 (FIG. 3D), the liquid FREON droplets rapidly become very cold as they evaporate. Humidity in the form of water molecules is usually present in the dry air or $O_2$ stream 24,38 (FIG. 3D). Such water molecules act as a source of heat which the cold FREON droplets absorb to continue evaporating. This results in condensation of gaseous water molecules into liquid water droplets that are absorbed by the medication particles as the FREON droplets rapidly evaporate. The liquid water absorbed by the medication particles then also evaporates rapidly, especially after most of the FREON evaporation has occurred. The assignee's laboratory tests have confirmed that medication particles which emerge from the distal end of the endotracheal tube 7 are far "drier" when the arrangement shown in FIG. 3D is used than if the plume 17 is ejected within the humid inspiratory path in the presence of inspiratory stream 1B. The medication particles, being drier and lighter than if plume 17 is ejected within the inspiratory stream 1B, are more efficiently carried to the patient's lungs.

The assignee's tests show that for the short amount of time (e.g., 30 seconds) required to administer an MDI dose, the dry gas has no harmful tendency to dry the lungs of the patient.

Referring to FIG. 5, an alternative embodiment of the invention is shown, wherein the manufacturer's MDI inhaler 12 is not used. Instead, an inline MDI aerosol dispensing nozzle device 31, somewhat similar to one described in commonly assigned U.S. Pat. No. 5,474,058 (Lix), entitled "MDI VENTILATOR DISPENSER WITH BI-DIRECTIONAL NOZZLE", issued Dec. 12, 1995, incorporated by reference herein, is connected between tube 22 carrying dry oxygen or air from the regulated source 23. Dispensing nozzle device 31 has an outlet tube 31A connected to the valved port 30A of the valved T connector 30 and a nozzle 30B into which the stem 14A of the canister 14 is inserted to introduce one or two plumes such as 17A and 17B in FIG. 5 into the volume dispensing nozzle device 31. The dry air/oxygen carried by tube 22 from the regulated source 23 into dispensing nozzle device 31 carries the medication particles of plumes 17A and 17B into inspiratory stream 1B and prevents exposure of dry MDI particles to excessive moisture from the humid inspiratory stream 1B.

Figure 6A:
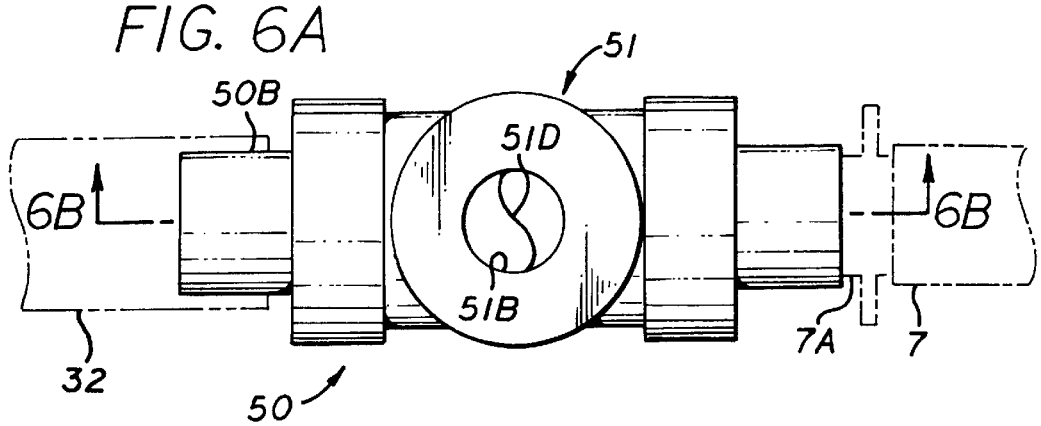
Figure 6B:
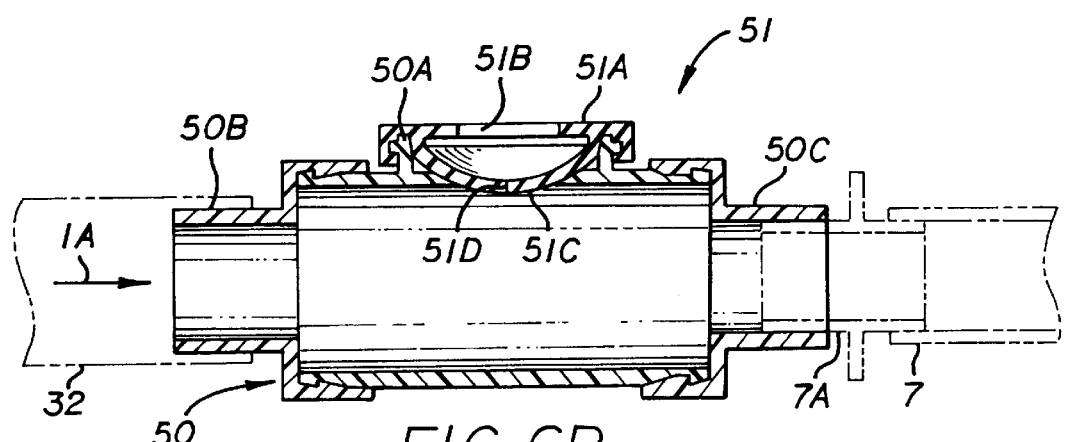

Referring to FIGS. 6A and 6B, an alternate valved T connector 50 is shown, having an inlet port 50B to which the inspiratory tube 32 is connected and an outlet port 50C to which the adapter 7A of endotracheal tube 7 is connected. Valved T connector 50 has a medication inlet port 50A onto which an elastic valve 51 is attached, in a sealed manner. Valve 51 has an inner membrane 51A having a circular central opening 51B therein. The nozzle 26B of elastomeric adapter 26 of device 20 is inserted through opening 51B. An inner dome-shaped membrane 51C has an S-shaped slit 51D which acts as seal to prevent the pressurized inspiratory air stream 1B from escaping when the device 20 is not inserted, but separates an allows the nozzle to pass through the S-shaped slit 51D when the device of FIG. 3A is to be used to introduce a dose of MDI medication.

The invention substantially avoids the above mentioned problems caused by dry, light medication particles absorbing moisture from the inspiratory stream, gaining weight, and "falling out" of the inspiratory stream, and therefore more effectively delivers the desired dose of medication to the lungs of a patient. The invention also allows introduction of the medication downstream from the Y connector without substantially increasing "dead volume" from which air is rebreathed by the patient. The invention also allows the nozzle of inhalers provided with MDI canisters connected therein to be used to eject the plume of medication particles that are introduced into the inspiratory stream.

While the invention has been described with reference to several particular embodiments thereof, those skilled in the art will be able to make the various modifications to the described embodiments of the invention without departing from the true spirit and scope of the invention. It is intended that all elements or steps which are unsubstantially different or perform substantially the same function in substantially the same way to achieve the same result as what is claimed are within the scope of the invention.

Figure 7:
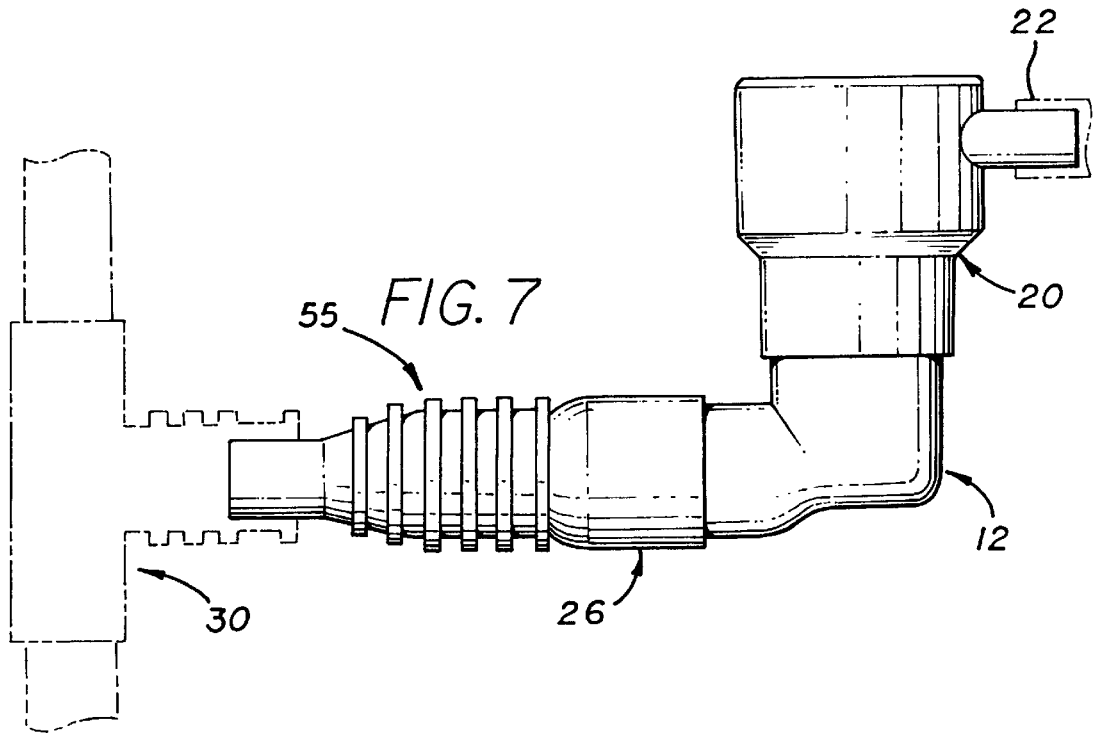

For example, a spacer 55 could be provided between inhaler 12 and valved T port 30A, as shown in FIG. 7, to allow more efficient conveying of plume 17 (FIG. 3D) into the inspiratory path. Also, a dry powder dispenser could be used to replace inhaler 12 in the arrangement of FIG. 3A. The valved port 3A could be configured to connect with the mouthpiece 12A of inhaler 12 without use of elastomeric coupler 26. Also, the valved T connector 30 could be coupled in line with the inspiratory tube 32 if no passive humidifier 6 (FIG. 1) is used between it and the endotracheal tube. As another example, the valved T connector 30 could be replaced by a different style of valved connector.

As another example, an inhaler supplied by the drug manufacturer including the MDI canister could be supported within a suitable housing or "cocoon" that is coupled in fluid communication with the inspiratory stream to carry a bolus of dry air or oxygen and the ejected plume of medication particles into the inspiratory stream. Also, the bolus of dry air or oxygen could be produced other than from a constant flow source, for example by means of a bellows, piston, syringe, or the like. As yet another example, connector 30 does not necessarily have to be a valved port. That is, a T coupler with a removable cap on the port corresponding to 30A could be provided; then, when it is desired to couple adapter 26 to the connector, the cap could be removed and section 26B of coupler 26 could be quickly inserted into the unvalved port within less than a second so that the exposure of the inspiratory stream to airborne contamination would be minimal.

What is claimed is:

1. Apparatus for introducing a measured dose of minute, dry medication particles into an inspiratory stream of a ventilator system including an inspiratory tube, a Y connector, and an endotracheal tube intubated in a patient, the apparatus comprising:
    (a) a connector having an inlet port and first and second ports coupled to conduct the inspiratory stream through the connector;
    (b) a medication dispensing device actuatable to eject a plume constituting a measured dose of minute, dry medication particles, the medication dispensing device including a mouthpiece, an internal nozzle structure for electing an expanding plume of medication particles toward the mouthpiece, a boot portion having an open end in fluid communication with the mouthpiece, and an MDI canister within the boot portion and having a stem inserted into an inlet of the nozzle structure; and
    (c) a closed plume-containing structure receiving an expanding plume of minute dry medication particles from the mouthpiece, the plume-containing structure having a first port for insertion into the inlet port to direct the expanding plume to flow through the inlet port into the inspiratory stream, through the endotracheal tube, and into the lungs of the patient.

2. Apparatus for introducing a measured dose of minute, dry medication particles into an inspiratory stream of a ventilator system including an inspiratory tube, a Y connector, and an endotracheal tube intubated in a patient, the apparatus comprising:
    (a) a connector having an inlet port and first and second ports coupled to conduct the inspiratory stream through the connector;
    (b) a medication dispensing device actuatable to eject an expanding plume constituting a measured dose of minute, dry medication particles; and
    (c) a closed plume-containing structure receiving the expanding plume of minute dry medication particles from the medication dispensing device, the plume-containing structure having a first port for insertion into the inlet port and a dry gas inlet coupled to a dry gas source and directing dry gas through the plume-containing structure to carry the expanding plume through the inlet port into the inspiratory stream, through the endotracheal tube, and into the lungs of the patient, the dry gas reducing absorption of moisture in the inspiratory stream by the medication particles.

3. Apparatus for introducing a measured dose of minute, dry medication particles into an inspiratory stream of a ventilator system including an inspiratory tube, a Y connector, and an endotracheal tube intubated in a patient, the apparatus comprising:
    (a) a valved connector having a valved inlet port and first and second ports coupled to conduct the inspiratory stream through the valved connector;
    (b) a medication dispensing device actuatable to eject an expanding plume constituting a measured dose of minute, dry medication particles; and
    (c) a closed plume-containing structure for receiving the expanding plume of minute dry medication particles from the medication dispensing device, the plume-containing structure having a first port for insertion into the valved inlet port and a dry gas inlet coupled to a dry gas source and directing dry gas through the plume containing structure to carry the expanding plume through the valved inlet port into the inspiratory stream, through the endotracheal tube, and into the lungs of the patient, the dry gas reducing absorption of moisture in the inspiratory stream by the particles.

4. Apparatus for introducing a dose from a metered dose inhaler canister into the inspiratory stream of a ventilator system including an inspiratory tube, a Y connector, and an endotracheal tube intubated in a patient, the apparatus comprising:
    (a) a valved connector having a valved port and first and second ports coupled to conduct the inspiratory stream through the valved connector;

(b) an MDI canister; and (c) a nozzle adapter structure having a first port for insertion into the valved port to open a valve thereof, an internal nozzle structure for receiving a stem of the MDI canister and ejecting an expanding plume of medication particles upon activation of the MDI canister, a second port for receiving the expanding plume, and a dry gas inlet coupled to a dry gas source and directing dry gas through the nozzle adapter structure into the valved port and into the inspiratory stream;

the dry gas carrying the expanding plume from the nozzle adapter structure through the valved port into the inspiratory stream, through the endotracheal tube into the lungs of the patient, the dry gas reducing absorption of moisture in the inspiratory stream by the particles.

5. Apparatus for introducing a dose from a metered dose inhaler (MDI) into the inspiratory stream of a ventilator system including an inspiratory tube, a Y connector, and an endotracheal tube intubated in a patient, the apparatus comprising:

(a) a valved T connector having a valved port and first and second ports coupled to conduct the inspiratory stream through the valved T connector;

(b) a metered dose inhaler including a mouthpiece, an internal nozzle structure for ejecting a plume of medication particles toward the mouthpiece, a boot portion having an open end in fluid communication with the mouthpiece, and an MDI canister within the boot portion and having a stem inserted into an inlet of the nozzle structure;

(c) a coupler having a first port for insertion into the valved port to open a valve thereof and a second port for coupling to the mouthpiece; and (d) an end cap disposed on the open end of the boot portion, the end cap including a dry gas inlet coupled to a dry gas source and guiding dry gas to flow through the boot portion, mouthpiece, and coupler into the valved port and into the inspiratory stream, the end cap including a depressible portion for transmitting an actuation force to the MDI canister to cause it to inject propellant containing medication particles into the nozzle structure and thereby causing the nozzle to eject an expanding plume of medication particles from which the propellant evaporates, the dry gas carrying the plume through the coupler into the valved port and into the inspiratory stream, through the endotracheal tube into the lungs of the patient, the dry gas reducing absorption of moisture from the inspiratory stream by the medication particles.

6. The apparatus of claim 5 wherein the valved T connector is located between the Y connector and the endotracheal tube.

7. The apparatus of claim 5 wherein the valved port includes a valve which automatically opens when the coupler is inserted and automatically closes when the coupler is withdrawn from the valved T port.

8. The apparatus of claim 5 wherein the coupler and the end cap are disposed of elastomeric material, the depressible member including a flexible membrane over the open end of the boot portion.

9. The apparatus of claim 5 wherein the flow rate of the inspiratory stream is in the range of 25 to 125 liters per minute, and the dry gas flow rate is in the range of 8 to 15 liters per minute.

10. The apparatus of claim 5 wherein the dry gas inlet is integral with the end cap.

11. A method for introducing a measured dose of minute, dry medication particles into an inspiratory stream of a ventilator system including an inspiratory tube, a Y connector, and an endotracheal tube intubated in a patient, the method comprising:

(a) providing a valved connector having a valved inlet port, and first and second ports coupled to conduct the inspiratory stream through the valved connector;

(b) actuating a medication dispensing device to eject a plume constituting a measured dose of minute, dry medication particles into a closed plume-containing structure, the plume-containing structure having a first port and a dry gas inlet coupled to a dry gas source;

(c) inserting the first port into the valved inlet port; and (d) causing dry gas to flow and carry the plume through the valved inlet port into the inspiratory stream, through the endotracheal tube, and into the lungs of the patient, the dry gas reducing absorption of moisture in the inspiratory stream by the particles.

12. A method for introducing a dose from an MDI inhaler into the inspiratory stream of a ventilator system including an inspiratory tube, a Y connector, and an endotracheal tube intubated in a patient, the method comprising:

(a) providing a T connector having an inlet port, and first and second ports coupled to conduct the inspiratory stream through the T connector;

(b) enclosing (1) a mouthpiece of the MDI inhaler including an internal nozzle structure for ejecting a plume of MDI medication particles, a boot portion having an open end in fluid communication with the mouthpiece, and an MDI canister within the boot portion and having a stem inserted into an inlet of the nozzle structure, and a second port for insertion into the inlet port, and (2) the open end of the boot portion; and (c) depressing a depressible portion of material enclosing the open end of the boot portion to transmit an actuation force to the MDI canister to cause it to inject a metered dose of propellant containing medication particles into the nozzle and thereby causing the nozzle to eject an expanding plume of the medication particles from which the propellant evaporates, the plume moving through the inlet port into the inspiratory stream, through the endotracheal tube into the lungs of the patient.

13. A method for introducing a dose from an MDI inhaler into the inspiratory stream of a ventilator system including an inspiratory tube, a Y connector, and an endotracheal tube intubated in a patient, the method comprising:

(a) providing a valved T connector having a valved port, and first and second ports coupled to conduct the inspiratory stream through the valved T connector;

(b) placing a first port of a coupler on a mouthpiece of an MDI inhaler including an internal nozzle structure for ejecting a plume of MDI medication particles, a boot portion of the MDI inhaler having an open end in fluid communication with the mouthpiece, and an MDI canister within the boot portion and having a stem inserted into an inlet of the nozzle structure, the coupler having a second port for insertion into the valved port to open a valve thereof;

(c) placing an end cap on the open end of the boot portion, the end cap including a dry gas inlet for coupling to a dry gas source;

(d) causing dry gas to flow from the dry gas source through the dry gas inlet into and through the boot portion and the mouthpiece through the valved port and into the inspiratory stream; and (e) depressing a depressible portion of the end cap to transmit an actuation force to the MDI canister to cause it to inject a metered dose of propellant containing MDI particles into the nozzle structure and thereby causing the nozzle to eject an expanding plume of MDI particles from which the propellant evaporates, the dry gas carrying the plume through the open valved port into the inspiratory stream, through the endotracheal tube into the lungs of the patient, the dry gas reducing absorption of moisture from the inspiratory stream by the MDI particles.

* * * * *